United States Patent
Gabrielson et al.

(10) Patent No.: US 9,446,991 B2
(45) Date of Patent: *Sep. 20, 2016

(54) COMPOSITIONS OF SUBSTANTIALLY SPHERICAL PARTICLES AND METHODS OF MAKING THEREOF

(71) Applicant: Koch Agronomic Services, LLC, Wichita, KS (US)

(72) Inventors: Kurt D Gabrielson, Lilburn, GA (US); Stacey L Wertz, Conyers, GA (US); Drew R Bobeck, Doraville, GA (US); Allen R Sutton, Corydon, KY (US)

(73) Assignee: Koch Angronomic Services, LLC, Wichita, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/671,337

(22) Filed: Mar. 27, 2015

(65) Prior Publication Data
US 2015/0203413 A1    Jul. 23, 2015

Related U.S. Application Data

(63) Continuation of application No. 13/968,330, filed on Aug. 15, 2013, now Pat. No. 9,034,072.

(51) Int. Cl.
| | |
|---|---|
| C05C 9/02 | (2006.01) |
| C05B 15/00 | (2006.01) |
| C05C 1/00 | (2006.01) |
| C07F 9/22 | (2006.01) |
| C05G 3/00 | (2006.01) |
| C05G 3/08 | (2006.01) |

(52) U.S. Cl.
CPC ............ *C05C 9/02* (2013.01); *C05B 15/00* (2013.01); *C05C 1/00* (2013.01); *C05G 3/0041* (2013.01); *C05G 3/0058* (2013.01); *C05G 3/08* (2013.01); *C07F 9/224* (2013.01)

(58) Field of Classification Search
None
See application file for complete search history.

(56) References Cited

U.S. PATENT DOCUMENTS

| | | | | | |
|---|---|---|---|---|---|
| 3,248,255 | A | * | 4/1966 | Belasco | A23K 1/22 426/312 |
| 3,477,842 | A | * | 11/1969 | Cook | B01J 2/30 252/384 |
| 4,530,714 | A | * | 7/1985 | Kolc | C05G 3/08 71/28 |
| 9,034,072 | B2 | * | 5/2015 | Gabrielson | C05B 15/00 71/28 |
| 2003/0154754 | A1 | * | 8/2003 | Costa | C05C 9/02 71/28 |
| 2004/0035162 | A1 | * | 2/2004 | Williams | C05B 17/00 71/28 |
| 2007/0157689 | A1 | * | 7/2007 | Sutton | C05C 9/00 71/28 |
| 2012/0156275 | A1 | * | 6/2012 | Lambeth | A01N 25/26 424/409 |
| 2013/0174623 | A1 | * | 7/2013 | Gabrielson | C05C 9/005 71/29 |
| 2015/0031786 | A1 | * | 1/2015 | Lambeth | C08L 61/24 523/132 |

\* cited by examiner

*Primary Examiner* — Wayne Langel

(57) ABSTRACT

An improved composition comprising substantial spherical UFP particles and an active agent, such as NBPT, and optionally other components is used as an additive for liquid and solid fertilizers, typically containing urea. Methods of making the compositions and their use are also disclosed.

17 Claims, 1 Drawing Sheet

COMPOSITIONS OF SUBSTANTIALLY SPHERICAL PARTICLES AND METHODS OF MAKING THEREOF

CROSS-REFERENCE TO RELATED APPLICATION

This application is a continuation of U.S. application Ser. No. 13/968,330 filed Aug. 15, 2013, which claims priority under 35 U.S.C. §119(e) from U.S. Provisional Application 61/683,319, filed Aug. 15, 2012.

BACKGROUND OF THE INVENTION

Fertilizers have been used for some time to provide nitrogen to the soil. Commercial fertilizers can come in a variety of liquid or solid forms. The most widely used and agriculturally important liquid form of nitrogen fertilizer is urea ammonium nitrate (UAN) and the most widely used and agriculturally important solid form is granular urea, a white crystalline solid under normal conditions. Urea is a commonly used nitrogen fertilizer due to its relatively low cost and its high nitrogen concentration (46%). Solid forms of urea, include granular, prilled, pelletized, powdered or dust. Normally, the granular form is somewhat larger in particle size than the prills. Most of the urea-based fertilizer currently used is produced in its granular form.

After urea is applied to soil, it is hydrolyzed to yield ammonia and carbon dioxide. This process is catalyzed by the enzyme urease, which is an extracellular enzyme in the soil. The gaseous products formed by the hydrolysis reaction (ammonia and carbon dioxide) volatilize to the atmosphere and thus, substantial losses from the total amount of the nitrogen applied to the field occur. Accordingly, some solid, water soluble fertilizers can be made slow release by various additives. For example, the hydrolysis process can be considerably decelerated by applying enzyme inhibitors, specifically urease or nitrification inhibitors with urea. Examples of urease inhibitors are the thiophosphoric triamide compounds disclosed in the U.S. Pat. No. 4,530,714, including N-(n-butyl)thiophosphoric triamide (NBPT). NBPT is used in a number of agricultural products, such as AGROTAIN® and AGROTAIN ULTRA® (see e.g. U.S. Pat. No. 5,698,003) and SUPER N® (see e.g. U.S. Pat. No. 5,364,438) and SUPER U®, UFLEXX® and UMAXX® (see e.g. U.S. Pat. No. 5,352,265).

Industrial grade N-(n-butyl)thiophosphoric triamide (NBPT) is a solid, waxy and sticky compound, that decomposes in water and at elevated temperatures. Accordingly, its direct application onto urea particles is very difficult. In some applications, PERGOPAK® M by the Albemarle Corporation (which is made by the process disclosed in U.S. Pat. No. 6,936,078) has been used as a carrier for NBPT (see U.S. Patent Publication 2007/0157689). NBPT is deposited into the PERGOPAK® M by first dissolving the NBPT in NMP and then drying the NBPT and PERGOPAK® M mixture to form a solid. This solid is then blended with granulated urea. An alternative form of this product can be made by applying the molten NBPT directly to the PERGOPAK® M and then subsequently blending this with granulated urea.

However, the combination of NBPT with PERGOPAK®M can result in several problems making its use difficult. The combination can form large clumps which must be filtered out before use. This leads to poor product yield. The combination can also have difficulty flowing through equipment, which leads to poor consistency of application levels on urea. The combination is also dusty and has an undesirable odor. These issues can lead to variations in NBPT ratios when formulating the mixture of NBPT and PERGOPAK® M with granulated urea. Because of variations in the NBPT levels, formulators may need to add a significant excess of the NBPT/PERGOPAK® M formulation to form a commercial, granulated urea formulation. In addition, there are also safety challenges in managing the dust levels at formulation facilities. Further, the mixture of NBPT and PERGOPAK® M has limited long-term stability and can typically only be stored in containers smaller than or including a fiber drum in order to minimize decomposition.

Accordingly, there remains a need for new compositions and methods of improving the properties of urea-based fertilizers coated with other active agents. The present invention as described herein addresses this and other needs by providing a formulation of urease or nitrification inhibitors with a urea-formaldehyde polymer as disclosed in U.S. Pat. No. 6,936,681. The formulation of the present invention significantly improves the flow of the mixture comprising the urease inhibitor, thereby reducing dust, increasing bulk density and providing more uniform formulated product.

BRIEF SUMMARY OF THE INVENTION

The present invention relates to a composition comprising an active agent and substantially spherical particles. The present invention also relates to methods of making the compositions and their use in agricultural applications.

DETAILED DESCRIPTION OF THE INVENTION

Figure 1A:
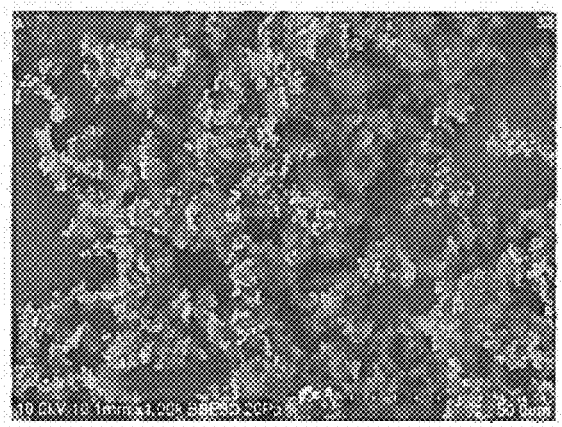
FIGS. 1A and 1B are 1000× magnification photographs showing the difference in morphology of particles comprising PERGOPAK® M (FIG. 1A) and NITAMIN 36S (FIG. 1B) with NBPT in accordance with the present invention.
Figure 1B:
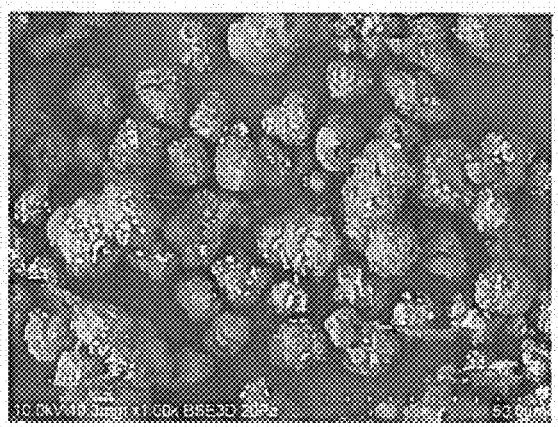

As noted above, the present invention is directed to compositions that comprise a substantially spherical particles. In one group of embodiments, the substantially spherical particles are urea-formaldehyde (UF or ureaform) polymer (UFP) particles) that are useful in agricultural applications. The invention specifically relates the use of the substantially spherical UFP particles with an active agent. In one embodiment, the composition comprises from about 30% to 70% of an active agent and from about 70% to about 30% by weight of substantially spherical particles of a urea-formaldehyde polymer based on the total weight of the composition.

All percentages, parts and ratios are based upon the total weight of the compositions of the present invention, unless otherwise specified. All such weights as they pertain to listed ingredients are based on the active level and, therefore, do not include solvents or by-products that may be included in commercially available materials, unless otherwise specified. The term "weight percent" may be denoted as "wt. %" herein. All molecular weights as used herein are weight average molecular weights expressed as grams/mole, unless otherwise specified.

As used herein, "substantially" is intended to indicate a range of up to about 20% of any value indicated.

The term "substantially spherical" as used herein means that the material has a morphology that includes spherical, as well as oblong, and the like and can have surface irregularities. The sphericity of a particle can be determined using image analyzer which identifies and measures a particles image in the form of a sphere, and calculates the sphericity of a particle, as Da/Dp (where Da=(4A/π); Dp=P/π; A=pixel area; P=pixel perimeter), is a value from zero to one, with one representing a sphere. For example, in some embodiments, the particle can have a sphericity of about 0.8 or more, about 0.81 or more, about 0.82 or more, about 0.83 or more, about 0.84 or more, about 0.85 or more, about 0.86 or more, about 0.87 or more, about 0.88 or more, about 0.89 or more, about 0.9 or more, about 0.91 or more, about 0.92 or more, about 0.93 or more, about 0.94 or more, about 0.95 or more, about 0.96 or more, about 0.97 or more, about 0.98 or more, or about 0.99 or more.

Substantially Spherical UFP Particles

The substantially spherical urea-formaldehyde polymer (UFP) particles of the present invention are those disclosed in U.S. Pat. No. 6,936,681, which is incorporated in its entirety herein by reference. Non-limiting examples of urea-formaldehyde polymers suitable for use in the practice of the present include those sold under the name NITAMIN 36S® by Koch Agronomic Services, LLC.

Process for Making Substantially Spherical UFP Particles

The substantially spherical UFP particles of the present invention are prepared by reacting, in an aqueous environment, urea and formaldehyde at a urea:formaldehyde mole ratio of about 1:1. To prepare the UFP particles of the present invention, urea and formaldehyde are reacted in admixture at a mole ratio of approximately 1:1, for example at a UF mol. ratio broadly in the range of 0.7:1≤U:F≤1.25:1 and or in the range of 0.83:1≤U:F≤1.1:1. The phase "at a mole ratio of approximately 1:1" is intended to embrace these mole ratio ranges. Particularly good results have been obtained at a U:F mole ratio between 0.95:1 and 1.05:1.

In the initial step of preparing the substantially spherical UFP particles, reaction between urea and formaldehyde is conducted in a manner to produce methylol ureas. For example, reaction between the urea and formaldehyde can be promoted by maintaining the aqueous mixture initially at a moderate alkaline pH, with a pH in the range of about 7 to 9 being suitable and with a pH more usually between about 7.5 and 8.5, to promote the formation of methylol ureas. Given urea's inherent level of alkalinity, any required pH adjustment may be accomplished using either an acid or a base. The initial formation of methyol ureas generally can be conducted at a reaction temperature broadly in the range of 70° F. to 175° F. (about 20° C. to about 80° C.) with a reaction temperature in the range of 90° F. to 160° F. (about 30° C. to about 70° C.) more usually employed. The pH may be adjusted using commonly available acids and bases such as sodium hydroxide (caustic) and sulfuric acid and any material that can alter the pH is suitable for this purpose. The reaction pH also may be maintained (buffered) or adjusted by adding such alkaline compounds as triethanolamine, sodium or potassium bicarbonate, sodium or potassium carbonate, or other alkali metal hydroxides, such as potassium hydroxide and lithium hydroxide. Alternatively, the methylolation may also be done at a moderate acidic pH, such as in the pH range of 5.0 to 6.0, as will be recognized by those skilled in the art and the present invention is not limited by the way the initial methylolation is conducted.

Following the initial formation of methyol ureas, the nascent UFP then is condensed to the point where the polymer becomes insoluble in the aqueous environment. This result can be accomplished by rapidly acidifying the methylol ureas, to a pH below about 6, usually below about 5 and usually to a pH below about 4, but above about 1. A pH in the range of 2.5 to 4.0 has proven to be suitable. Any organic or inorganic acid that will lower the pH can be used. Particularly suitable is a strong acid, such as a mineral acid and an organic acid such as the stronger carboxylic acids. Thus, suitable acids include formic acid, acetic acid, nitric acid, phosphoric acid, sulfuric acid and hydrochloric acid. However, in its broadest aspects the present invention is not limited by the way the further polymerization of the methylol ureas and ultimate insolubilization is conducted and obtained.

In order to produce a desired range of substantially spherical UFP particle diameters, the aqueous mixture of the methylol ureas is mixed in the presence of a dispersing agent during the step of rapid polymerization which leads to insolubilization, such as the rapid acidification step, although it is possible to get a similar result by maintaining a sufficiently high level of agitation (high shear) during the reaction in the absence of any dispersing agent. The resulting dispersion of UFP formed from the polymerization that occurs, for example, following acidification, is then recovered or isolated from the dispersion to produce substantially spherical UFP particles, which then are used in any of the various applications noted herein. The substantially spherical UFP particles formed in this manner have approximately 36% by weight nitrogen when dry.

Skilled practitioners recognize that the formaldehyde and urea reactants used to make the substantially spherical UFP particles of this invention are commercially available. The formaldehyde used can be in any available form. Paraform (solid, polymerized formaldehyde) and formalin solutions (aqueous solutions of formaldehyde, sometimes with methanol, in 37 percent, 44 percent, or 50 percent formaldehyde concentrations) are commonly used sources of formaldehyde. Formaldehyde also may be available as a gas. Each of these sources of formaldehyde is suitable for use in the preparing the substantially spherical UFP particles of this invention. Generally, for ease of use, formalin solutions are used as the formaldehyde source, in addition, some of the formaldehyde may be replaced with another aldehyde, such as acetaldehyde and/or propylaldehyde that can react with urea. Glyoxal may also be used in place of formaldehyde, as may other aldehydes not specifically enumerated.

Urea also is available in many forms. Solid urea, such as prill, and urea solutions, typically aqueous solutions, are commercially available. Further, urea often is chemically combined with formaldehyde in the form of a urea-formaldehyde concentrate, such as UFC 85, or as a commercially-available solution containing about 25 weight percent urea, about 60 weight percent formaldehyde, and about 15 weight percent water, available under the trademark STA-FORM 60®. In one embodiment the urea formaldehyde source is UFC 85. Each of these sources of urea and formaldehyde can be used in preparing the substantially spherical UFP particles of this invention.

The urea-formaldehyde condensation reaction that results in the substantially spherical UFP particles of this invention may be conducted in an aqueous environment. As noted above, the reaction is conducted until the growing urea-formaldehyde polymer becomes insoluble in the aqueous reaction medium. A dispersing agent may be included in the water to facilitate the production of small polymer particles by the reaction. One suitable dispersant is the line of DAXAD® dispersants commercially available from Hampshire Chemicals, a subsidiary of the Dow Chemical Company. One of the classes of these dispersants is a condensed naphthalene sulfonate. Both the high and low molecular weight species of this product line have been shown to be suitable, such as DAXAD 19. A variety of other dispersants or surfactants also can be used, including those that might be classified as anionic, such as polyacrylates (also available under the DAXAD® label-such as DAXAD 30 from Hampshire Chemicals). Nonionic and cationic dispersant compounds also can be used. The nature of the specific dispersant/surfactant is not critical. Another example is a lignosulfonate salt or lignin. It is also possible to dispense with the use of any dispersant, provided that the reaction medium is sufficiently agitated (high shear) during the UF condensation reaction to promote the formation of small substantially spherical UFP particles.

The amount of dispersant to include in the aqueous solution of methylol urea at the time of the insolubilization reaction can be readily determined by those skilled in the art. The amount depends to some extent on the particular dispersant chosen to use and the concentration of methylol urea in the aqueous reaction medium. Generally, the urea and formaldehyde reactants and the water vehicle are provided in amounts to yield a methylol urea concentration that ultimately provides a dispersion of UFP at about a 20% by weight solid concentration up to about 60% by weight solids. More usually, the materials are provided so that the UFP dispersion is between about 30% and 55% by weight solids. In one embodiment, the dispersion UFP is prepared at about a 40% by weight solids concentration. Under these conditions, the dispersing agent is generally supplied at a concentration of between about 0.1% and 5% by weight, and usually in at least about 0.5% by weight up to about 2% by weight.

In the broad practice of this invention, the aqueous dispersion of UFP is isolated to form substantially spherical UFP particles before use. According to the broadest aspects of the invention, any way for isolating the substantially spherical UFP particles from the aqueous substantially spherical UFP particles dispersion can be used. For example, the substantially spherical UFP particles in the dispersion may be isolated by filtration and oven drying, or by thin film evaporation. When using these latter techniques, it may then be necessary to reduce the particle diameter of the recovered solids, for example by grinding, to obtain a desired particle diameter or diameter distribution for a specific application.

In one embodiment, the way of isolating or recovering the substantially spherical UFP particles from the dispersion formed by the polymerization of urea and formaldehyde as described above, is by spray-drying. As used herein, the terms "spray dryer" and "spray drying" refer to the technically sophisticated process of atomizing (in the form of finely divided droplets) the UFP dispersion or slurry into a gas stream (often a heated air stream) under controlled temperature conditions and under specific gas/liquid contacting conditions to effect evaporation of water from the atomized droplets and production of a dry particulate solid product. Spray drying as used herein is typically carried out with pressure nozzles (nozzle atomization) or centrifugal atomizers operating at high speeds (e.g., a spinning disc). Despite the high velocity generation of droplets, a spray dryer is designed so that the droplets do not contact the spray dryer wall under proper operating procedures. This effect is achieved by a precise balance of atomizer velocity, air flow, spray dryer dimensions of height and diameter, and inlet and outlet means to produce a cyclonic flow of gas, e.g., air in the chamber. A pulse atomizer also can be used to produce the small droplets needed to facilitate evaporation of the water. In some cases, it may be desirable to include a flow promoter, such as an aluminosilicate material, in the aqueous dispersion that is processed in a spray dryer simply to facilitate subsequent handling and transport of the spray dried substantially spherical UFP particles (e.g., to avoid clumping).

The shape and size of the substantially spherical UFP particles is fairly consistent. Producing substantially spherical UFP particles of a consistent size helps adhere the desired amount or active as well as other components subsequent formulations. By using the method of making the substantially spherical UFP particles in the presence of a dispersant, it is easy to produce most of the substantially spherical UFP particles of a consistent size so as to pass through a 100 mesh (U.S. or Tyler) screen, and generally at least a major portion pass through a 200 mesh screen. Thus, the majority of the substantially spherical UFP particles with have a diameter larger than about 0.15 micrometers. In one group of embodiment, the substantially spherical UFP particles will have a diameter smaller than about 150 microns and a larger than about 10 microns. As a practical matter, the majority of particles will have a diameter in the range of between about 10 microns, 20 microns, 30 microns, 40 microns, 50 microns, 60 microns, 70 microns, 80 microns, 90 microns, 100 microns, 110 microns, 120 microns, 130 microns, 140 microns and 150 microns. A number average particle diameter of about 30 microns is common, but portion may be below 10 microns.

The term "majority" as used herein means the greater number or part; a number more than half the total. For example, in some embodiments, majority can mean about 51% or more, about 52% or more, about 53% or more, about 54% or more, about 55% or more, about 56% or more, about 57% or more, about 58% or more, about 59% or more, about 60% or more, about 60% or more, about 61% or more, about 62% or more, about 63% or more, about 64% or more, about 65% or more, about 66% or more, about 67% or more, about 68% or more, about 69% or more, about 70% or more, about 71% or more, about 72% or more, about 73% or more, about 74% or more, about 75% or more, about 76% or more, about 77% or more, about 78% or more, about 79% or more, about 80% or more, about 81% or more, about 82% or more, about 83% or more, about 84% or more, about 85% or more, about 86% ore, about 86% or more, about 87% or more, about 88% or more, about 89% or more, about 90% or more, about 91% or more, about 92% or more, about 93% or more, about 94% or more, about 95% or more, about 96% or more, about 97% or more, about 98% or more, about 99% or more.

Thus, in the broad practice of this invention, the isolated, substantially spherical UFP particles, recovered from the aqueous dispersion, for example by spray-drying, then is used in combination with active agents and in further applications.

While not wishing to be bound by theory, the inventors hereof believe morphology of the substantially spherical UFP particles is directly attributable to the conditions of the above-process. Also, the inventors believe morphology of the substantially spherical UFP particles not only facilitates its coating by the active agent(s) but also improves the properties of further formulations. Because of its uniformity in size and shape, the composition of the substantially spherical UFP particles has significantly less dust which avoids the need for further dust control agents, which can cause undesirable properties, such as clumping in subsequent formulations.

Compositions of a Substantially Spherical UFP Particle and an Active Agent

Active Agents

"Active agent" as used herein is meant to refer to compounds, chemicals, etc., that finds use in agricultural applications and are commonly applied to urea-formaldehyde polymers. Non-limiting examples of active agents suitable for use herein include materials commonly used in fertilizer applications that are not toxic to seeds, or harmful to the soil environment in which seeds are planted, or in which a plant is growing. Such materials may include urease or nitrification inhibitors, pesticides, herbicides and fungicides to combat or prevent undesired insects, weeds and disease. Mixtures of these different materials may of course also be employed. In one group of embodiments, described in more detail hereafter, one or more of these materials is combined with the substantially spherical UFP particles of the invention to produce granular fertilizer solids.

In one group of embodiments of the invention, the substantially spherical UFP particles are used with a urease inhibitor, a nitrification inhibitor or a pesticide, such as a fungicide, an insecticide, or a herbicide. Urease inhibitor, as used herein, is meant to refer to compounds that interfere with urease activity and reduce urea hydrolysis in soils. In one group of embodiments the active agent is a urease inhibitor. Examples of urease inhibitors include, but are not limited to, phosphoric triamides, such as N-(n-butyl)thiophosphoric triamide (NBPT) and the like. In another group of embodiments, the urease inhibitor is N-(n-butyl)thiophosphoric triamide ("NBPT"). The NBPT can be crude or pure (with less than 10% other ingredients). In some embodiments, the NBPT is purified by recrystallization.

Nitrification inhibitors are compounds which inhibit the conversion of ammonium to nitrate and reduce nitrogen losses in the soil. Examples of nitrification inhibitors include, but are not limited to, dicyandiamide (DCD), and the like. The DCD of the present invention can have a particle size in the range from about 50 to 350 µm. The DCD is present in the dry flowable additive in the range of about 0.01 to 99%, or about 40 to 95%, or 70 to 90%. In a further embodiment of the invention, the dry flowable additive may contain from about 1.0 to 30.0% substantially spherical UFP particles and from about 40 to 90% DCD. Without DCD, the composition may contain about 1 to 80% NBPT and about 99 to 20% of the substantially spherical UFP particles. The ratio of NBPT to DCD should exceed a value of about 0.02, in some embodiments is be between about 0.02 and about 10.0, and in some embodiments is between about 0.04 and about 4.0. In one embodiment the composition comprises about 81% DCD, about 8% UFP, and about 11% of a NBPT/UFP mixture. In some embodiments only one active agent, as described above, is used.

The utilization of both a urease inhibitor and a nitrification inhibitor, in the fertilizer composition of this invention offers an opportunity to tailor the make-up of the composition to match the nitrogen nutrient demand of a given crop/soil/weather scenario. For example, if the soil is characterized by a low pH and/or if rain is anticipated shortly after fertilizer application and the opportunity for ammonia losses through volatilization to the atmosphere is thereby diminished, the level of the NBPT urease inhibitor incorporated into the formulation may be reduced, within the specified range, without also changing the level of the DCD (nitrification inhibitor). The relative resistance of the fluid fertilizer composition of this invention to urea hydrolysis and ammonia oxidation is controlled by properly selecting the NBPT to DCD weight ratio of the composition. This ratio should exceed a value of about 0.01, or between about 0.02 and about 8.0, or be between about 0.05 and about 1.0. Fluid fertilizer compositions with NBPT to DCD weight ratios near the higher end of these ranges will exhibit relatively higher resistance to urea hydrolysis than to ammonium oxidation, and vice versa. This independent control over the relative resistance of the composition to urea hydrolysis and ammonia oxidation is unattainable through the methods of prior art and provides unparalleled flexibility in meeting the nutrient demands of various crops under a broad range of soil/weather conditions.

Process for Making Compositions of a Substantially Spherical UFP Particle and an Active Agent The means by which the one or more active agents are deposited onto the substantially spherical UFP particles can be selected from any method known. In one group of embodiments, the one or more active agents are deposited onto the substantially spherical UFP particles by using a blending or drying device such as a high shear mixer, ribbon blender, blade mixer, or other similar device. While heat need not be applied during blending, in one group of embodiments, the drying device is a ribbon blender or blade blender. In other embodiments, the composition is blended in standard blending equipment without drying equipment.

Typically, one or more active agents are coated onto or mixed with the substantially spherical UFP particle by introducing into the drying or blending device the substantially spherical UFP particles and a solution comprising a solvent and the one or more active agents. Another embodiment is to blend the substantially spherical UFP particles with the active ingredient/ingredients without solvent present. In another embodiment, molten NBPT is directly sprayed onto the substantially spherical UFP particles while mixing. The mixture is then subsequently dried at an elevated temperature.

The amount of substantially spherical UFP particle used with any particular urease inhibitor may vary and will usually depend on the particular application, as well as the optional presence of other components besides the substantially spherical UFP particle used in the present invention. The composition comprising the one or more active agents typically contains from about 30 to about 80 wt. % of the active agent, based on the weight of the composition, of the one or more active agent(s). In one group of embodiments, the composition comprises from about 40 to 70 wt. %, based on the total weight of the composition. In one group of embodiments, the composition comprises from about 50 to about 60 wt. % of the active agent based on the total weight of the composition.

In the practice of this embodiment of the present invention, the substantially spherical UFP particles and active agent solution can be introduced into the drying device simultaneously, in stages, either the substantially spherical UFP particle solution introduced before the other, or any combinations thereof. Thus, this embodiment of the present invention can be either a batch or continuous process. In one group of embodiments, the active agent solution is introduced into the drying device after the substantially spherical UFP particles. In this and other embodiments, the introduction of the active agent solution is controlled to avoid over-wetting of the substantially spherical UFP particles. Over-wetting can be prevented by introducing the active agent solution into the drying device at a rate substantially equal to the rate at which the solvent volatilizes. The volatilization of the solvent is achieved by operating the drying device under conditions that include a temperature that is below the melting point of the active agent(s) and below the boiling point of the solvent. In one group of embodiments, the drying device is operated under such a temperature and a sub-atmospheric pressure. In one group of embodiments, the temperatures under which the drying device is operated are in the range of from about 20° C. to about 200° C., or in the range of from about 20° C. to about 100° C., or from about 20° C. to about 50° C. Also, as stated above, the drying device may be operated under sub-atmospheric pressures, i.e. under a vacuum. These pressures may be in the range of from about 760 mmHg to about 0.1 mmHg, or in the range of from about 500 mmHg to about 50 mmHg, or from about 100 mmHg to about 50 mmHg.

Other Optional Agents

Other optional components may be used in compositions of the present invention. Examples of other agents, include but are not limited to a conditioner, xanthan gum, calcium carbonate (agricultural lime) in its various forms for adding weight and/or raising the pH of acid soils; metal containing compounds and minerals such as gypsum, metal silicates and chelates of various micronutrient metals such as iron, zinc and manganese; talc; elemental sulfur; activated carbon, which may act as a "safener" to protect against potentially harmful chemicals in the soil; a plant protectant; a nutrient stabilizer, super absorbent polymers, wicking agents, wetting agents, plant stimulants to accelerate growth, an inorganic nitrogen, phosphorus, potassium (N—P—K) type fertilizer, sources of phosphorus, sources of potassium, and organic fertilizers, surfactants, initiators, stabilizers, cross linkers, antioxidants, UV stabilizers, reducing agents, dyes, such as blue dye (FD & C blue #1); and plasticizers. Examples of conditioners include but are not limited to tricalcium phosphate, sodium bicarbonate, sodium ferricyanide, potassium ferricyanide, bone phosphate, sodium silicate, silicon dioxide, calcium silicate, talcum powder, bentonite, calcium aluminum silicate, stearic acid, and polyacrylate powder. Examples of plant protectants and nutrient stabilizers include silicon dioxide, and the like.

The content of the additional components can be from about 1 to about 99 percent by weight of the composition. For example, the amount of the additional components in the composition can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or about 99% by weight of the total granular fertilizer composition.

Fertilizer Compositions
Solid Urea-based Fertilizer Compositions
Urea Fertilizer Base The urea-based granular fertilizer of the present invention can include any suitable quantity of a urea source and contains one or more additional components. In one group of embodiments, the urea source is granulated solid or prilled urea. One of skill in the art will appreciate other urea sources for the inventive methods. The amount of the urea source in the urea-based granular fertilizer can range from about 1% to about 99% by weight of the total granular fertilizer composition. The amount of the urea source in the urea-based granular fertilizer can be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or about 99% by weight of the total granular fertilizer composition In another group of embodiments, the present invention provides a urea-based granular fertilizer composition comprising:
a) a urea source of from about 95% to 99% by weight of the total granular fertilizer composition;
b) a composition of an active agent and substantially spherical UFP particles as described above in the range of from about 1% to 5% by weight of the total granular fertilizer composition.

Thus in one embodiment, the urea content of the composition of this invention is between about 90% and about 99% by weight, and alternatively between about 92% and about 99% by weight. The content of the NBPT and substantially spherical UFP particle composition is between about 0.02% and about 0.5% by weight, or between about 0.04% and about 0.4% by weight. DCD may account for about 0.01% to about 90% by weight of the composition, and in some embodiment's accounts for between about 0.05% and about 81% by weight of the composition. The composition may also contain some moisture, urea synthesis byproducts, and an NBPT solvent of this invention, and as noted above may optionally contain other additives, such as a dye, an NBPT stabilizer, or a micronutrient. The diameter of the granules of the improved homogenous urea-based fertilizer composition of this invention ranges from about 0.5 millimeters to about 10 millimeters, and in some embodiments from about 0.8 millimeters to about 0.9, to about 1.0, to about 1.1, to about 1.2, to about 1.3, to about 1.4, to about 1.5, to about 1.6, to about 1.7, to about 1.8, to about 1.9, to about 2.0, to about 2.1, to about 2.2, to about 2.3, to about 2.4, to about 2.5, to about 2.6, to about 2.7, to about 2.8, to about 2.9, to about 3.0, to about 3.1, to about 3.2, to about 3.3, to about 3.4, to about 3.5, to about 3.6, to about 3.7, to about 3.8, to about 3.9, to about 4.0, to about 4.1, to about 4.2, to about 4.3, to about 4.4, to about 4.5, to about 4.6, to about 4.7, and to about 4.8 millimeters.

Processes for Making Solid Urea-based Fertilizer Compositions

In one aspect, the present invention provides a method, wherein the contacting is selected from the group consisting of blending and mixing. The conditioner when mixed or blended with a urea-based fertilizer provides a urea-based fertilizer that has improved storage and handling properties.

In one group of embodiments, the present invention provides a composition similar to wherein commercial fertilizers, including, but not limited to SUPER U®; UFLEXX®; UMAXX®; or granular urea treated with AGROTAIN DRY® except that substantially spherical UFP particles are used as the UFP component.

In one group of embodiments, the NBPT/substantially spherical UFP particle composition can be incorporated into the homogenous urea-based fertilizer composition by blending, either dry or as a concentrated solution of NBPT/substantially spherical UFP in a solvent directly on urea. The incorporation can be done at ambient conditions or on molten urea at a temperature of about 266° F. to about 275° F. prior to the granulation or prilling of the urea in a conventional urea production facility. Sufficient mixing is employed during this blending step to assure that the NBPT/substantially spherical UFP solution is homogeneously distributed, especially before the melt cools and solidifies in the subsequent granulation step if molten urea is used.

The amount of the active agent and substantially spherical UFP particle compositions of the present invention added to urea in accordance with this invention in either solid or liquid form depends on the desired NBPT content of the granular fertilizer composition and can be readily calculated by those skilled in the art. In some embodiments, no or only very limited quantities of a solvent are introduced into the urea along with the NBPT and substantially spherical UFP particle composition. For example, if the NBPT and substantially spherical UFP particle composition content of the concentrated NBPT solution used to incorporate the NBPT and substantially spherical UFP particle composition in the fertilizer composition is 70% and the NBPT content of the resulting fertilizer composition is 0.07%.

In some embodiments, DCD can be added to and blended with the urea at this point in the formulation rather than during the formulation with substantially spherical UFP particles, alone. Several methods can be used for the introduction of DCD into solid or molten urea: if available as a powder or in granular form, the DCD can be fed into a stream of solid or molten urea using a conventional solids feeding device; or, the DCD may be dissolved in a relatively small quantity of molten urea, as for example in a side stream of molten urea in a urea plant, to form a concentrated DCD solution in molten urea which is then metered into the main stream of the solid or molten urea. Finally, the DCD may be incorporated into a solution of the NBPT and substantially spherical UFP particle composition described hereinabove and introduced into the urea or molten urea along with the NBPT and substantially spherical UFP particle composition. Regardless of the method selected to introduce the DCD into the urea, sufficient mixing should be provided to facilitate homogenous distribution of the DCD throughout the urea. The homogeneous distribution of the NBPT, the substantially spherical UFP particle and DCD in the granular fertilizer compositions of this invention enhances the performance of these compositions in terms of their ability to promote plant growth.

The order in which the NBPT and substantially spherical UFP particle composition and the DCD are added to the urea in the practice of this invention is flexible: either the NBPT and substantially spherical UFP particle composition or DCD may be introduced first, or both of these components may be added simultaneously. In one group of embodiments, the DCD is added first to provide adequate time for both the dissolution and uniform distribution of the DCD in the molten urea prior to the granulation step. A convenient point for the addition of DCD to urea in a urea production plant is before or between any evaporation steps used to reduce the water content of the urea. The NBPT and substantially spherical UFP particle composition, however, may be introduced into the molten urea just prior to the granulation or prilling step with only sufficient retention time in the melt to allow for uniform distribution of the NBPT in the melt. In one group of embodiments, the retention time of the melt between the point of the NBPT and substantially spherical UFP particle composition addition and the granulation step is less than 5 minutes, or less than 1 minute.

After the NBPT and substantially spherical UFP particle composition is combined with the urea, the granules may be sized. In one group of embodiments, granules which pass through a 4 mesh Tyler Series sieve (about 4.76 millimeters) and stay on a 20 mesh Tyler Series sieve (about 0.84 millimeters) are retained as product. The undersized particles may be recycled and the oversized particles may be ground and/or recycled.

Liquid Urea-based Compositions

The present invention also provides an improved fluid urea-ammonium nitrate (UAN) fertilizer composition containing the NBPT and substantially spherical UFP particle composition. Specifically, the improved fluid fertilizer composition of this invention is comprised primarily of an aqueous solution of urea, ammonium nitrate, the NBPT and substantially spherical UFP particle composition, and optionally dicyandiamide (DCD).

The urea content of the composition of this invention is between about 24% and about 32% by weight, or between about 26% and about 32% by weight; the ammonium nitrate content of the composition is between about 34% and about 42% by weight, or between about 36% and about 42% by weight; the NBPT content of the composition is between about 0.01% and about 0.4% by weight, or between about 0.02% and about 0.3% by weight; and the DCD accounts for about 0% to about 2.0% by weight of the composition, and may account for between about 0.03% and about 1.5% by weight of the composition. The balance of the composition consists primarily of water. A solvent for the NBPT as disclosed above, may also be present in small quantities.

In accordance with the present invention, the NBPT and substantially spherical UFP particle composition may be incorporated into the fluid fertilizer composition by adding a solid or liquid form of the NBPT and substantially spherical UFP particle composition directly to a UAN fluid with sufficient mixing to assure that the NBPT is homogeneously distributed throughout the fluid fertilizer composition. Both the solid and liquid forms of the NBPT and substantially spherical UFP particle composition as disclosed above can be introduced into UAN using conventional metering devices.

The amount of the NBPT and substantially spherical UFP particle composition in accordance with this invention depends on the desired NBPT content of the fertilizer composition within the ranges specified herein above and on the NBPT content of the concentrated NBPT solution, and can be readily calculated by those skilled in the art.

Like the solid formulation, DCD can also be added to the UAN fluid at this stage, rather than with the substantially spherical UFP particles, alone. Several methods are available for the introduction of DCD into UAN. If available as a powder or in granular form, the DCD can be fed into UAN fluid using a conventional solids feeding device. In one group of embodiments, however, the DCD is first incorporated into a relatively small quantity of VAN fluid so as to form a slurry of DCD in UAN fluid; this slurry is then blended with the balance of the UAN fluid in the amount needed to provide the desired concentration of DCD within the ranges specified hereinabove. Regardless of the method selected to introduce the DCD into the UAN fluid, sufficient mixing should be provided to facilitate homogenous distribution of the DCD throughout the UAN fluid. The homogeneous distribution of both the NBPT and substantially spherical UFP particle composition and DCD in the fluid fertilizer compositions of this invention enhances the performance of these compositions in terms of their ability to promote plant growth.

The order in which the NBPT and substantially spherical UFP particle composition and DCD are added to the fluid fertilizer in the practice of this invention is flexible: either the NBPT and substantially spherical UFP particle composition or DCD may be introduced first, or both of these components may be added simultaneously. However, in light of the relative instability of NBPT in aqueous solutions, solid or liquid forms of the NBPT and substantially spherical UFP particle composition may be introduced into the fluid fertilizer relatively late in production-storage-distribution sequence of the fluid fertilizer, so as to minimize the time span between the addition of the NBPT and substantially spherical UFP particle composition to the fluid fertilizer and the application of the fertilizer to the soil.

Processes for Making Liquid Urea-Based Compositions

The NBPT and substantially spherical UFP particle composition is added to the UAN solution in the range of about 0.1 to 5.0% additive in the final product. In one group of embodiments, the NBPT and substantially spherical UFP particle composition is added in the range of about 0.4 to 2.5% to fluid UAN or urea solution, or blends thereof, to form a fluid fertilizer. The fluid urea-based fertilizer of the present invention contains from about 0.004 to 1.50% NBPT, from about 0 to 0.850% DCD, from about 0.030 to about 0.30% substantially spherical UFP particles, and from about 99.9 to 98.0% aqueous UAN. Optionally, the fertilizer can contain up to about 0.03% silicon dioxide. The aqueous UAN contains urea and ammonium nitrate in concentration ranges of about 15 to 50%. In one group of embodiments, the range is from about 25 to 40%.

Use

The granular fertilizer composition of this invention made by the methods described herein can be used in all agricultural applications in which granular fertilizer compositions are currently used. These applications include a very wide range of crop and turf species, tillage systems, and fertilizer placement methods. The fertilizer granules made with the NBPT and substantially spherical UFP particle composition of present invention are useful for fertilizing a wide variety of seeds and plants, including seeds used to grow crops for human consumption, for silage, or for other agricultural uses. Indeed, virtually any seed or plant can be treated in accordance with the present invention using the compositions of the present invention, such as cereals, vegetables, ornamentals, conifers, coffee, turf grasses, forages and fruits, including citrus. Plants that can be treated include grains such as barley, oats and corn, sunflower, sugar beets, rape, safflower, flax, canary grass, tomatoes, cotton seed, peanuts, soybean, wheat, rice, alfalfa, sorghum, bean, sugar cane, broccoli, cabbage and carrot.

The granular urea-based fertilizer composition of this invention can be used in all agricultural applications in which granular urea is currently used. These applications include a very wide range of crop and turf species, tillage systems, and fertilizer placement methods. Most notably, the fertilizer composition of this invention can be applied to a field crop, such as corn or wheat, in a single surface application and will nevertheless supply sufficient nitrogen to the plants throughout their growth and maturing cycles. The fertilizer composition of this invention is capable of supplying the nitrogen nutrient with greater efficiency than any previously known fertilizer composition. The new improved composition increases the nitrogen uptake by plants, enhances crop yields, and minimizes the loss of both ammonium nitrogen and nitrate nitrogen from the soil.

The rate at which the fertilizer composition of this invention is applied to the soil may be identical to the rate at which urea is currently used for a given application, with the expectation of a higher crop yield in the case of the composition of this invention. Alternately, the composition of this invention may be applied to the soil at lower rates than is the case for urea and still provide comparable crop yields, but with a much lower potential for nitrogen loss to the environment. It is of interest to illustrate the quantities of NBPT and DCD introduced into the soil when a given composition of this invention is applied as a fertilizer. For example, assuming that the composition is applied to the soil at a rate of 100 pounds per acre and that it contains 0.1% NBPT and 1% DCD, it can be readily calculated that the rates of NBPT and DCD application are 0.1 and 1.0 pounds per acre, respectively.

The UAN-based fluid fertilizer composition of this invention can be used in all agricultural applications in which UAN is currently used. These applications include a very wide range of crop and turf species, tillage systems, and fertilizer placement methods.

The UAN-based fertilizer composition of this invention can be used in all agricultural applications in which UAN is currently used. These applications include a very wide range of crop and turf species, tillage systems, and fertilizer placement methods. The fertilizer composition of this invention can be applied to a field crop, such as corn or wheat, in a single surface application and will nevertheless supply sufficient nitrogen to the plants throughout their growth and maturing cycles. Moreover, the fluid fertilizer composition of this invention supplies nitrogen nutrient to crop plants with greater efficiency than any previously known fluid fertilizer composition. The new improved composition increases the nitrogen uptake by plants, enhances crop yields, and minimizes the loss of both ammonium nitrogen and nitrate nitrogen from the soil.

The rate at which the fertilizer composition of this invention is applied to the soil may be identical to the rate at which UAN is currently used for a given application, with the expectation of a higher crop yield in the case of the composition of this invention. Alternately, the composition of this invention may be applied to the soil at lower rates than is the case for UAN and still provide comparable crop yields, but with a much lower potential for nitrogen loss to the environment. It is of interest to illustrate the quantities of NBPT and DCD introduced into the soil when a given composition of this invention is applied as a fertilizer. For example, assuming that the composition is applied to the soil at a rate of 200 pounds per acre and that it contains 0.05% NBPT and 0.5% DCD, it can be readily calculated that the rates of NBPT and DCD application are 0.1 and 1.0 pounds per acre, respectively.

The following examples are intended to illustrate, but not to limit, the methods and compositions of the invention. All percentages described herein are by weight, unless otherwise indicated.

EXAMPLE 1

Spray-Dried Substantially Spherical UFP Particles

A urea-formaldehyde (UF) dispersion, suitable for producing substantially spherical UFP particles used in the present invention, is prepared as follows. Water (32.3 parts by weight) and a 50% aqueous solution of formaldehyde (31.8 parts by weight) were added to a reaction vessel equipped with vacuum reflux, a heater and a mixer. While adjusting the temperature of the agitated aqueous mixture to 100° F., its pH is also adjusted to about 7.0 (6.8 to 7.2) using either 50% caustic (NaOH), or 35% sulfuric acid, as needed. Once the aqueous mixture was heated to 100° F. (about 38° C.), 31.8 parts by weight of prilled urea also was added and mixing was continued. The temperature of the agitated aqueous mixture then was increased to 120° F. (about 50° C.) and held for a time (usually about 15 minutes) sufficient to dissolve the urea. While maintaining the temperature of the agitated mixture at 120° F. (about 50° C.), the pH is adjusted to within the range of 8.0 to 8.4, again using either 50% caustic (NaOH), or 35% sulfuric acid as needed. Using, as appropriate, a combination of the reaction exotherm and external heating, the reaction mixture was heated to a temperature of 158° F. and the temperature is controlled using vacuum reflux. The pH of the mixture was adjusted, as needed, to about 7.8 to 8.2, using either 50% caustic (NaOH), or 35% sulfuric acid. The agitated mixture was held at a temperature of about 158° F. (70° C.) for about 30 minutes and the pH was adjusted, as needed, to about 7.8 to 8.2, using either 50% caustic (NaOH), or 35% sulfuric acid so that the reactants formed methylol ureas. While continuing agitation, the aqueous mixture was cooled to about 105° F. (about 40° C.) and a dispersant (one part by weight of DAXAD 19) was added while the batch was cooled. Upon reaching 105° F. (about 40° C.), the batch was placed under full vacuum. While maintaining full vacuum and applying cooling to the agitated batch, the pH of the aqueous mixture was adjusted, as quickly as possible, to a pH of about 3.3 to 3.5, using 35% sulfuric acid, at which point the batch may exotherm to a temperature of above 175° F. (about 80° C.) before the exotherm subsides. This procedure caused rapid condensation of the methylol ureas to a solid network polymer. After completing the pH adjustment, the temperature of the aqueous mixture was cooled to 105° F. (about 40° C.) as quickly as possible while it was held for 20 minutes. Following the 20 minute holding period, the pH of the aqueous mixture was adjusted to 6.5 to 7.5, using either 50% caustic (NaOH), or 35% sulfuric acid, as needed, and then was discharged to storage. The UFP dispersion at about 38 weight percent solids was agitated during its storage.

The dispersion above can then be spray dried to produce UF polymer particles. A Niro P6 spray dryer can be fed with 15 pounds per hour of the dispersion of Example 1. The spray dryer receives an inlet gas stream at a flow rate of about 415 standard cubic feet per minute and a temperature of 330-340° F. (165-170° C.). The outlet temperature of the spray dryer was measured as 75-95° F. (25-35° C.). The recovered UF polymer particle product (at about 1 wt. % moisture) had particle diameter distributed from 10 to 80 microns, with a number average diameter of 30 microns.

ALTERNATIVE EXAMPLE 1

Spray-Dried UFP

Using a Niro industrial-sized spray dryer (ON 030-5051), a UF polymer dispersion made in accordance with Example 1 having about a 38 wt. % solids content, at a temperature of 28° C. and at a feed rate of 100 lbs/minute was spray-dried with the atomizer wheel operating at 13,000 RPMs. Air, at a flow rate of 49,400 standard cubic feet per minute and at a temperature of 186° C. was delivered to the spray dryer. The outlet air temperature was measured as 88° C. Spray-dried UF polymer particles were recovered from the spray dryer.

ALTERNATIVE EXAMPLE 2

Spray-Dried UFP

A UF polymer dispersion made in accordance with Example 1 using 45.27 wt. % water 25.7 wt. % UFC 85. While adjusting the temperature of the agitated aqueous mixture to about 30° C., its pH is also adjusted from about 6.7 to 7.3 using either 50% caustic (NaOH), or 35% sulfuric acid, as needed. Once the aqueous mixture was heated to about 30° C., 24.423 wt. % prilled urea also was added and mixing was continued. The temperature of the agitated aqueous mixture then was increased to about 50° C. and held for a time (usually about 15 minutes) sufficient to dissolve the urea. While maintaining the temperature of the agitated mixture at about 50° C., the pH is adjusted to within the range of 8.0 to 9.0, again using either 50% caustic (NaOH), or 35% sulfuric acid as needed. Using, as appropriate, a combination of the reaction exotherm and external heating, the reaction mixture was heated to a temperature of about 70° C. and the temperature is controlled using vacuum reflux. The pH of the mixture was adjusted, as needed, to about 7.8 to 8.2, using either 50% caustic (NaOH), or 35% sulfuric acid. The agitated mixture was held at a temperature of about 70° C. for about 30 minutes and the pH was adjusted, as needed, to about 7.8 to 8.2, using either 50% caustic (NaOH), or 35% sulfuric acid so that the reactants formed methylol ureas. While continuing agitation, the aqueous mixture was cooled to about 40° C. and a dispersant (one part by weight of DAXAD 19) was added while the batch was cooled. Upon reaching about 40° C., the batch was placed under full vacuum. While maintaining full vacuum and applying cooling to the agitated batch, the pH of the aqueous mixture was adjusted, as quickly as possible, to a pH of about 3.1 to 3.5, 20% ammonium sulfate, at which point the batch may exotherm to a temperature of above about 80° C. before the exotherm subsides. This procedure caused rapid condensation of the methylol ureas to a solid network polymer. After completing the pH adjustment, the temperature of the aqueous mixture was cooled to about 40° C. as quickly as possible while it was held for 20 minutes. Following the 20 minute holding period, the pH of the aqueous mixture was adjusted to 6.5 to 7.5, using 20% ammonium sulfate, as needed, and then was discharged to storage. The UFP dispersion at about 38 weight percent solids was agitated during its storage. This material was spray dried as above.

COMPARATIVE EXAMPLE 3

PERGOPAK® M with NBPT
(N-n-butylthiophosphoric Triamide) from Albemarle Corp. with and without Mineral Oil A sufficient quantity of WFE bottoms (about 83% NBPT available from Albemarle® Corporation) is sprayed onto PERGOPAK®M, a urea formaldehyde polymer commercially available from the Albemarle® Corporation, to yield a precursor powder containing about 62 wt. % NBPT, 2 wt % of a dye (e.g. FD & C blue #1). The NBPT solution is blended into the PERGOPAK® M composition at 50° C. over a 30 minute period. The mixture is stirred for an additional 120 minutes to break up lumps until a uniform mix is achieved as indicated by the distribution of the dye. These steps can be repeated until sufficient NBPT solution has been loaded. Other components, such as DCD could also be blended during this process. After the addition is complete, 1% by weight mineral oil is optionally added to reduce dust. After this addition is complete the mixture is stirred for an additional 60 minutes to break up lumps. The mixture is allowed to air dry. The final weight of the PERGOPAK® M loaded with the NBPT is determined to be 100 g of as a compactable solid containing some agglomerates.

ALTERNATIVE COMPARATIVE EXAMPLE 4

PERGOPAK® M with NBPT from China with and without Mineral Oil

A 50% by weight solution of NBPT (available from Chinese source) solution in N-alkyl 2-pyrrolidone was added to 37 grams of PERGOPAK® M, a urea formaldehyde polymer commercially available from the Albemarle® Corporation, and 2 grams of a dye (e.g. FD & C blue #1). The NBPT solution was blended into the PERGOPAK® M at 25° C. over a 1 minute period. The mixture was stirred for an additional 14 minutes to break up lumps until a uniform mix was achieved as indicated by the distribution of the dye. These steps were repeated until sufficient NBPT solution had been loaded. Other components, such as DCD could also be blended during this process. After the addition was complete 1% by weight mineral oil was optionally added to reduce dust. After this addition was complete the mixture was stirred for an additional 0 minutes to break up lumps. The mixture was allowed to air dry. The final weight of the PERGOPAK® M loaded with the NBPT was determined to be 37 g (out of a total of 100 g) of as a compactable solid containing some agglomerates.

EXAMPLE 5

NITAMIN 36S with NBPT without Mineral Oil

A blend of NBPT (recrystallized or not recrystallized), Nitamin 36S UF powder, and green dye were made. The blends were made in a 35 cubic foot ribbon blender (Magnablend) which ran at approximately 16 rpm. Mineral oil was eliminated from the formulation because it reduced flow in PERGOPAK M formulations and the present formulation had reduced dust when compared to the PERGOPAK M formulation with oil. Any clumps of NBPT that were not incorporated into the Nitamin 36S UF powder were optionally removed from the final product via screening or broken up and reblended. The amount of moisture, the range of NBPT loading levels amongst particles, dust (tapped bulk density) and powder flow were measured for each batch by the running them through a vibrating funnel. The data is shown in the table below, where the data is an average of four batches:

| Composition | Amount in Drum (lbs) | Moisture (%) | NBPT loading level range | Tapped Bulk Density | Dry Flow Funnel Method (sec) |
|---|---|---|---|---|---|
| Comparative Example 3 | 150 | 2.73 | 60 | 26.8 | Did Not Flow |
| Alternative Comparative Example 4 | 110 | 5.02 | 60 | 16.0 | 31.3 |
| Example 5 | 200 | 1.69 | 60 | 31.1 | 4.6 |

This data demonstrates that the flow of the formulation of the present invention using NITAMIN 36S was dramatically better than that using PERGOPAK M. This formulation allowed for the formation of a product without the use of mineral oil. The powder flowed freely from the blender into the drums and bags. The formulation with PERGOPAK M, would not flow through the funnel at all.

As the data shows the compositions of this invention (Example 5) had a more uniform loading level and more efficient loading process, improved flow, and reduced dust (increased bulk density).

EXAMPLE 6

Comparative Examples with DCD

A blend of 6.53% NBPT, DCD, UFP and dye were made as in EXAMPLE 5, using the formulations in the table below:

| Composition | Example 6A | Example 6B |
|---|---|---|
| NBPT/UFP* | 12.56 (in NMP) | 10.89 |
| DCD | 81 | 81 |
| PERGOPAK M2 | 6.4 | 0 |
| NITAMIN 36S | 0 | 8.07 |
| DYE | 0.04 | 0.04 |

*Example 6A uses PERGOPAK M2 as UFP with NBPT, Example 6B uses Nitamin 36S as UFP with NBPT.

The additional amount of Nitamin 36S in Example 6B is optional. The primary advantage in Example 6B is that the NBPT is added to this formulation without the use of any solvents. Therefore, the final product is solvent-free. Formulation 6A uses a solvent. The amount of moisture, the range of NBPT loading levels amongst particles, dust (tapped bulk density) and powder flow were measured for each batch by the running them through a vibrating funnel. The moisture can be varied to some degree by the amount of heat put on the oven. The data is shown in the table below, where the data is an average of four batches:

| Composition | Amount in Drum (lbs) | Moisture (%) | NBPT loading level range | Tapped Bulk Density | 4-minute solubility test |
|---|---|---|---|---|---|
| Comparative Example 6A | 1500 | 4.8% | 6.5% | 42.1 | Passed |
| Example 6B | 1500 | 0-4 | 5.8-7 | 36-43 | Passed |

This data demonstrates that the moisture content and bulk density of the formulation of the present invention using NITAMIN 36S was dramatically better than that using PERGOPAK M.

EXAMPLE 7

Granular Urea Formulation with Formulation of EXAMPLE 5

As a first step, a 2000 g. batch of NBPT/UFP solution of Example 5 is pumped at a rate equivalent to 3 pounds of NBPT/UFP per 1997 pounds of urea into a 60 ton/hour stream of molten urea passing through a pipe leading from the last stage of urea evaporation directly to the urea granulation apparatus in a urea production facility. The temperature of the molten urea at the point at which the NBPT/UFP solution is injected is about 275° F. Although the retention time of the urea stream between the point at which the concentrated NBPT/UFP solution is injected and the urea granulation apparatus is only in the order of 20 seconds, the degree of turbulence in the stream of molten urea assures thorough mixing and homogenous distribution of the concentrated NBPT/UFP solution in the molten urea.

EXAMPLE 8

Granular Urea Formulation with Solid Formulation of NBPT and Nitamin 36S

This example illustrates the incorporation of the composition of Example 5 into a homogenous urea-based granular fertilizer composition. 1997 pounds of granulated urea is treated with 3 pounds of the solid composition of Example 5. The composition of Example 5 and urea are mixed in a blender until the fertilizer mixture is observed to flow freely.

The urea-based fertilizer is used directly or is stored.

EXAMPLE 9

Liquid Urea Formulation with Solid Formulation of NBPT and Nitamin 36S

This example illustrates the method of this invention for the incorporation of the NBPT/NITAMIN 36S composition into a fluid urea-containing fertilizer composition. The formulation of Example 5 was added at a rate equivalent to 2 pounds of NBPT/UFP per 1998 pounds of UAN solution into a 50 ton/hour stream of UAN solution containing 30% urea and 40% ammonium nitrate and approximately 10 pounds per ton DCD.

EXAMPLE 10

Liquid Urea Formulation with Liquid Formulation of NBPT and Nitamin 36S

This example illustrates the method of this invention for the incorporation of the NBPT/NITAMIN 36S composition into a fluid urea-containing fertilizer composition. The formulation of Example 5 was added at a rate equivalent to 2 pounds of NBPT/UFP per 1998 pounds of VAN solution into a 50 ton/hour stream of VAN solution containing 30% urea and 40% ammonium nitrate and approximately 10 pounds per ton DCD. Said stream of VAN solution was being transferred from a liquid storage tank into liquid rail cars. Although the retention time of the UAN solution between the point near the liquid storage tank at which the concentrated NBPT/UFP solution was injected into the UAN solution and the point at which the solution was discharged into the rail car was only in the order of 40 seconds, the degree of turbulence in the stream of VAN solution assured thorough mixing and homogenous distribution of the concentrated NBPT/UFP solution in the UAN solution. A set of rail cars was filled in this manner with a total of about 1400 tons of UAN solution containing about 0.1% NBPT.

Although the foregoing invention has been described in some detail by way of illustration and example for purposes of clarity of understanding, one of skill in the art will appreciate that certain changes and modifications may be practiced within the scope of the appended claims. In addition, each reference provided herein is incorporated by reference in its entirety to the same extent as if each reference was individually incorporated by reference. Where a conflict exists between the instant application and a reference provided herein, the instant application shall dominate.

What is claimed is:

1. A composition comprising
  a) from about 30% to about 70% of a solid active agent and
  b) from about 70% to about 30% by weight of substantially spherical urea-formaldehyde polymer (UFP) particles based on the total weight of the composition,
  wherein the solid active agent and the UFP particles are substantially adhered together, and
  wherein the active agent is N-(n-butyl)thiophosphoric triamide (NBPT).

2. A composition of claim 1, further comprising one or more components selected from the group consisting of a conditioner, a dye, and xanthan gum, wherein said one or more components are substantially adhered to said UFP particles.

3. A composition according to claim 2, wherein the conditioner comprises one or more components selected from the group consisting of tricalcium phosphate, sodium bicarbonate, sodium ferricyanide, potassium ferricyanide, bone phosphate, sodium silicate, silicon dioxide, calcium silicate, talcum powder, bentonite, calcium aluminum silicate, stearic acid, sodium aluminosilicate, and polyacrylate powder.

4. The composition of claim 1, wherein the substantially spherical UFP particles are made by acidifying a aqueous methylol urea solution, wherein the aqueous methylol urea solution is made by reacting urea and formaldehyde at a urea:formaldehyde mole ratio of from 0.7:1 to 1.25:1 and wherein the aqueous methylol urea solution either contains a dispersing agent or is subjected to a high shear condition during the acidifying (or both), to form an aqueous dispersion of insoluble urea-formaldehyde polymer particles and drying the dispersion to recover the urea-formaldehyde polymer particles.

5. The composition of claim 1, wherein a majority of the substantially spherical UFP particles have a particle diameter from about 10 microns to about 150 microns.

6. The composition of claim 1, made by a process comprising contacting the substantially spherical UFP particles with a mixture of said active agent and a solvent that is optionally selected from the group consisting of NMP, polyethylene glycol, and combinations thereof thereby forming said composition.

7. A composition of claim 1, further comprising urea, wherein said urea is present in an amount between about 90% and about 99% by weight, said active agent is present in an amount between about 0.02% and about 0.5% by weight.

8. The composition of claim 1, further comprising dieyandiamide and an aqueous solution of urea ammonium nitrate (UAN), wherein said urea is present in said aqueous solution in an amount between about 24% and about 32% by weight, said ammonium nitrate is present in an amount between about 34% and about 42% by weight, said active agent is present in an amount between about 0.01% and about 0.4% by weight, and said dieyandiamide is present in an amount of about 0.01% to about 2.0% by weight.

9. A composition of claim 7, wherein the composition is a granular fertilizer.

10. A composition of claim 9, wherein the diameter of the granules of said granular fertilizer ranges from about 0.80 to about 4.8 millimeters.

11. A composition of claim 1, further comprising dicyandiamide (DCD) in an amount of about 0.01% to about 90% by weight.

12. A composition of claim 7 or claim 8 prepared by blending or mixing the composition of claim 1 with the other components.

13. A composition of claim 1, wherein the active agent is in the form of solid particles that are substantially adhered to the UFP particles.

14. A composition of claim 1, made by a process comprising blending solid particles of the active agent with the substantially spherical UFP particles so that the solid particles of the active agent are substantially adhered to the UFP particles.

15. The composition of claim 1, further comprising a dye.

16. A composition comprising:
  a) solid NBPT in an amount of about 0.4% to about 15% by weight,
  b) substantially spherical urea-formaldehyde (UFP) particles in an amount of about 0.6% to about 40% by weight, and c) dicyandiamide (DCD) in an amount of from about 40% to about 95% by weight, wherein the solid NBPT and the UFP particles are substantially adhered together.

17. The composition of claim 16, further comprising a dye.

* * * * *